(12) United States Patent
Scheffer

(10) Patent No.: US 10,092,369 B2
(45) Date of Patent: Oct. 9, 2018

(54) METHOD FOR PRODUCING A DENTAL DRILLING TEMPLATE

(71) Applicant: med.dent.minds GmbH, Meerbusch (DE)

(72) Inventor: Axel Scheffer, Meerbusch (DE)

(73) Assignee: MED.DENT.MINDS GMBH, Meerbusch (DE)

( * ) Notice: Subject to any disclaimer, the term of this patent is extended or adjusted under 35 U.S.C. 154(b) by 0 days.

(21) Appl. No.: 15/306,794

(22) PCT Filed: Jun. 1, 2015

(86) PCT No.: PCT/EP2015/001110
§ 371 (c)(1),
(2) Date: Oct. 26, 2016

(87) PCT Pub. No.: WO2015/185205
PCT Pub. Date: Dec. 10, 2015

(65) Prior Publication Data
US 2017/0079744 A1  Mar. 23, 2017

(30) Foreign Application Priority Data
Jun. 3, 2014 (DE) .......... 10 2014 007 870

(51) Int. Cl.
*A61C 1/08* (2006.01)
*A61C 13/00* (2006.01)
(Continued)

(52) U.S. Cl.
CPC .......... *A61C 1/084* (2013.01); *A61B 6/02* (2013.01); *A61B 6/14* (2013.01); *A61C 1/085* (2013.01);
(Continued)

(58) Field of Classification Search
CPC ..... A61C 1/084; A61C 13/0022; A61C 1/085; A61C 13/0004; A61C 9/0046; A61B 6/02; A61B 6/14
See application file for complete search history.

(56) References Cited

U.S. PATENT DOCUMENTS 5,133,660 A * 7/1992 Fenick .............. A61B 6/14
433/173
5,556,278 A * 9/1996 Meitner .............. A61C 1/084
433/213
(Continued)

FOREIGN PATENT DOCUMENTS

DE 102010013411 A 12/2011

*Primary Examiner* — Ramesh Patel
(74) *Attorney, Agent, or Firm* — Andrew Wilford

(57) ABSTRACT

In order to make a custom dental drilling template, a single impression element is used that becomes a part of the later drilling template. To achieve this a guide-passage element is glued to the impression element. The exact position of the guide passage relative to the impression element prior to gluing is found by fixing both elements relative to each other on the same mounting plate using a periodic 2-D mounting structure. The passage element is mounted by an intermediate mounting element that is machined such that it carries the same or mating mounting structure according to positional data and that has a fitting area for fitting the guide passage to it.

10 Claims, 3 Drawing Sheets

(51) Int. Cl.
*A61B 6/02* (2006.01)
*A61B 6/14* (2006.01)
*A61C 9/00* (2006.01)

(52) U.S. Cl.
CPC ........ *A61C 9/0046* (2013.01); *A61C 13/0004* (2013.01); *A61C 13/0022* (2013.01)

(56) References Cited

U.S. PATENT DOCUMENTS

| | | | |
|---|---|---|---|
| 6,319,006 B1* | 11/2001 | Scherer | A61C 1/084 433/215 |
| 8,582,870 B2* | 11/2013 | Glor | A61C 1/084 382/154 |
| 9,378,308 B2* | 6/2016 | Pieper | A61C 1/084 |
| 9,566,137 B2* | 2/2017 | Hehn | A61C 9/0053 |
| 2007/0128581 A1 | 6/2007 | Moermann | |
| 2008/0254414 A1 | 10/2008 | McGuire | |
| 2010/0240000 A1* | 9/2010 | Yau | A61C 1/084 433/37 |
| 2010/0316974 A1* | 12/2010 | Yau | A61C 1/084 433/215 |
| 2010/0323324 A1 | 12/2010 | Kim | |
| 2011/0065065 A1 | 3/2011 | Moermann | |
| 2012/0202170 A1 | 8/2012 | Johnson | |
| 2012/0251979 A1 | 10/2012 | Karifm | |
| 2016/0144417 A1 | 5/2016 | Wu et al. | |

* cited by examiner

METHOD FOR PRODUCING A DENTAL DRILLING TEMPLATE

CROSS REFERENCE TO RELATED APPLICATIONS

This application is the U.S. national stage of PCT application PCT/EP2015/001110 filed 1 Jun. 2015 and claiming the priority of German patent application 102014007870.1 itself filed 3 Jun. 2014.

BACKGROUND OF THE INVENTION

The invention relates to a method of making a dental drilling template adapted to the jaw structure of a patient and having at least one guide passage for guiding a drilling tool and positioned in accordance with positional data on an impression element formed with a negative impression of the jaw structure.

Methods of this type are known in the prior art and are used in the field of implant technology. These methods are based primarily on x-raying the jaw of a patient and displaying it virtually as a model by a data-processing system so the position of an implant to be placed in the future and of the guide passage required therefor, along that a hole should be made in the patient's jawbone by a drilling tool in order to introduce an implant into the hole is specified on the basis of the displayed data. In this case the definition of the positional data usually takes place relative to a reference provided on an impression element held by the patient during the radiological recording of the jaw and is also recorded radiologically. Recording and subsequent display of the jaw to be treated can be carried out, for example by digital volume tomography.

Already in the prior art the virtual planning of the guide passage positioning is advantageously carried out in order, on the one hand, to locate an area with sufficient bone structure but also, on the other hand, to ensure that the holes provided for the implant placement do not damage any nerve pathways or other endangered neighboring structures.

Thus this positional data determined during the virtual planning is used to specify where to position a guide passage on an impression element having a negative impression of the patient's jaw structure. Such an impression element with at least one guide passage forms a drilling template in the context of the invention that is placed onto an existing jaw structure of a patient, according to which a dentist can drill a hole through the at least one guide passage.

DE 10 2010 031 018 [US 2013/0144417] discloses, for example, such a method in which a negative impression of the jaw structure including at least one guide passage as a whole is machined out of a blank with the aid of a computer. However, the method known in the prior art requires an elaborate and expensive machining apparatus, in particular a machine capable of creating guide passages, for example, as holes in the blank at any angular orientation. This can essentially only take place through time-consuming manual adjustment procedures on a multiaxis mounting base by experienced specialist staff or by an expensive five-axis machining apparatus.

For these reasons, the creation of such drilling templates that are thus formed substantially from an impression element having a negative impression of the jaw structure and at least one guide passage, can usually be carried out only by specialized machining centers. For the patients concerned, this means that long waiting times must be accepted, because their own dentists do not carry out the production of such drilling templates themselves.

OBJECT OF THE INVENTION

It is therefore an object of the invention to provide a method and means for carrying it out whereby the production of such drilling templates for assistance in the placement of implants can take place in a simple, fast and cost-effective manner, so that advantages for the patient are provided, namely shorter waiting times and also advantages for the attending dentists, namely the development of additional fields of activity and income resulting therefrom.

In particular, it is also an object of the invention to provide a method that allows the arbitrary positioning of guide passages on or in an impression element having a negative impression of the jaw structure with the aid of a less complex and expensive machining apparatus, such as for example a four-axis machine, as well as using already known working steps.

SUMMARY OF THE INVENTION

The object is achieved according to the invention in that the aforementioned generic method is further developed by the steps that a mounting body is manufactured that has an adapter and is adapted to the required position of the guide passage by machining of material by the machining apparatus, and a periodic closed mold mounting structure, preferably a closed mold mounting structure, in particular in at least two directions, is produced on the mounting body, during production in accordance with the positional data, and furthermore a passage element already comprising the guide passage, in particular in the form of a metallic sleeve and having an adapter that corresponds to the adapter of the mounting body, and in particular formed by the guide passage itself, is secured to the produced mounting body, after which the part formed by the mounting body and the passage element and comprising the closed mold mounting structure of the mounting body is fixed in a position calculated in accordance with the positional data, on a mounting plate comprising a corresponding closed mold structure, preferably in a periodic structure in at least two directions, the impression element is secured to the securing element opposite the mounting plate and the passage element is arranged, by fixing, in particular by an adhesive, on the impression element and by detaching from the mounting body to the impression element.

A closed mold mounting structure is understood to be a structuring of a surface on the mounting body that when the mounting body is attached to the mounting plate with the corresponding, preferably also planar structure forms a positive-locking configuration, so that as a result after fastening of these parts to one another the position of the mounting body on the mounting plate, in particular the orientation of the adapter thereof, is reliably fixed. The structure on the mounting body and the mounting plate can preferably be periodic in at least two directions (parallel to the plane of the surface that has the structure). In particular, the mounting structure on the mounting body can be identical to the structure on the mounting plate. The mounting structure and the structure on the mounting plate, particularly when they are identical to one another, are formed so that an inverted form/negative form of the structure in turn corresponds to the structure itself, and thus there is also an inversion identity.

The method according to the invention makes particular use here of the fact that a guide passage that is provided for later guiding of a drilling tool in or on the drilling template, does not actually have to be produced by a machining apparatus, but elements that are prefabricated or simple to produce are used. As a result, savings can already be made in terms of costs and working hours.

Furthermore, a machining apparatus for use in the method according to the invention functions with fewer degrees of freedom than one required according to the prior art for the production of guide passages at arbitrary angular orientations. In particular, not only a subtractively operating machining apparatus, such as for example a milling machine, but also an additive/generative machining apparatus can be used, such as for example a 3D printer.

According to the invention a passage element is used that already has a prefabricated guide passage, for example in the form of a metallic sleeve that can be surrounded, for example, by a plastic material, and according to the previously described steps, in the correct positioning, such a passage element is then brought by the mounting body and mounting plate into the required position relative to the impression element in order then to transfer the passage element to the impression element, specifically by fastening it to the impression element, for example by gluing, and the previous fastening to the mounting body is released.

In this case the required position and orientation or axial alignment of the guide passage is ensured by the orientation of the mounting structure of the mounting body that supports the passage element in a defined manner by the fit, and the fastening of the mounting body, by means of its closed mold mounting structure arranged thereon, on the corresponding structure of the mounting plate. In this connection the mounting structure is manufactured in the required situation relative to the adapter on the mounting body, in particular as a function of the positional data that define the required position of a guide passage.

The manufacture of a mounting body can take place, for example, by removal of material. A mounting body blank can be provided, for example, as a plastic block that already has an adapter and is machined by removal of material so that the required mounting structure is produced, that is to say is machined out of the blank. Furthermore, for this purpose a mounting body blank can also have a grippable element by which the mounting body blank can be clamped in a machining apparatus.

Alternatively, it is also possible to produce a mounting body by means of an additive/generative manufacturing technique, for example by application of material by 3D printing. Both plastic and also metal materials can be used here. Both the mounting structure, that is to say also the adapter, and a region connecting these regions can be produced generatively as a component.

In addition to the step according to the invention of manufacturing the mounting body for an individual patient, a passage element can also be manufactured for an individual patient, for example manufactured from a passage element blank that already comprises the guide passage, in particular also as a function of the positional data and, for example, again removal of material by a machining apparatus.

In this connection according to the invention the machining of a passage element blank and/or mounting body blank takes place with the same machining apparatus, for example a four-axis milling machine in which a blank is gripped by a grippable element provided on the blank.

Also, a passage element can also be produced here by generative manufacture, for example by so-called 3D printing, from plastic or metal. In this case it may be provided that the guide passage, like the entire passage element, is produced generatively, in particular preferably in a metal design. Also, an existing metallic sleeve can be enclosed by plastic by generative manufacture in a machining apparatus.

For the purpose of determining positional data, as is known in the prior art, the jaw of a patient to be treated may be recorded radiologically, for example by digital volume tomography. For this purpose, the invention may provide that an impression element is produced with a negative impression of the jaw structure of the patient to be treated, which later becomes part of the drilling template to be produced.

Here it is a further advantage, for example, by comparison with the prior art referred to above, that for the creation of an impression element known cost-effective techniques can be used, for example taking an impression of a jaw structure is performed by a molding compound or the molding of a plaster model of the jaw by a deep-drawn film, in particular where undercuts on the patient's bite or on the model are filled before application of the compound or the deep-drawn film.

According to the invention an impression element already used initially for the radiological recording can be used for a later component of the drilling template according to the invention, by fastening at least one passage element precisely to this impression element.

Furthermore, the invention provides that the impression element is provided with a radiological reference, in particular an X-ray reference, in order to be recorded radiologically in conjunction with a reference for the positional data, after positioning of the impression element in or on the patient's jaw region.

Then on the basis of software the position of a guide passage can be specified in a virtual display of the patient's jaw structure that takes place relative to the reference that is fastened to the impression element. The mounting body and/or passage element are manufactured as a function of the positional data.

For the purpose of transferring the passage element to the impression element, the invention can preferably provide that the impression element is fastened to such a fastening element on the mounting plate directly or indirectly by an accessory that simultaneously comprises a radiological reference, in particular an X-ray reference.

Thus such a fastening element can be fixed on the impression element and thus can be used both for the radiological recording of the patient's jaw and also for the later fastening directly or indirectly by accessories to the mounting plate, which simultaneously ensures that by the virtual relative positioning of the guide passage relative to the radiological reference a positioning relative to the mounting plate also takes place automatically if the position of the mounting plate with respect to the radiological reference is known and fixed.

In order to ensure this, the fastening element may be brought into reproducible engagement with the mounting plate or accessories fastened thereon.

For example, fastening of the impression element by the fastening element to the mounting plate or an accessory fastened thereto can take place in that the fastening element has metal elements, for example metal pins that can be inserted into corresponding recesses or holes on the mounting plate or the accessory arranged thereon. An accessory may be, for example, a planar element that is fastened to the mounting plate, spaced apart therefrom and parallel thereto, in particular where the planar element has a recess and in particular as a result takes the form of a planar frame.

Here the metal elements, in particular the metal pins, form the radiological reference. The fastening element can be designed, for example, as a vestibular arc that surrounds the push-out element on the outer face thereof.

The invention also comprises the possibility of reproducing the relationship of the model to the mounting plate by a frame assembly. This is advantageous, since then the planar accessory arranged with a spacing parallel to the mounting plate and/or the vestibular X-ray reference can be taken off without loss of orientation. Thus the surfaces of the mounting plate covered by this accessory are freed for mounting of the mounting bodies. At the same time the model is correctly situated for checking. For production of this frame assembly the reference is first of all produced in the manner described above and then the mounting plate is replaced by a mounting plate of the frame assembly that simultaneously forms the removable upper part of the frame assembly, and an individual plaster base is produced for the correct position of the model on the base plate.

The invention can provide that by radiological image recording, in particular by tomographic imaging techniques such as for example digital volume tomography, with the accessory of software a virtual model of a patient's jaw is produced and a virtual guide passage is positioned relative to the virtual jaw model and to the reference, and positional data that determine the position of the closed mold mounting structure on the mounting body are formed from the identified positional data of the at least one virtual guide passage. Then, with reference to these positional data that determine the position of the closed mold mounting structure on the mounting body, a machining apparatus can manufacture the mounting body with the required location of the mounting structure, for example from a blank.

A particularly preferred embodiment of the method according to the invention can provide that the closed mold mounting structure on the mounting body and/or the closed mold structure on the mounting plate is formed as tapered projections arranged at a uniform spacing adjacent one another in at least two directions.

Such projections can be formed, for example, as pyramidal projections with at least three, preferably four side faces inclined relative to one another, and in particular the base faces thereof touch one another.

Such projections can also be produced as conical projections.

Such a choice of the closed mold mounting structure/ structure is advantageous here, particularly in the case of manufacture from blanks with removal of material, since even with a simple machining apparatus having only four axes such structures can be arranged in planes that have the most varied angles relative to the extension axes from the guide passage or adapter.

In this case a plane in which the projections are arranged is understood to be such a plane in which the same regions of all projections, that is to say for example all tips of the projections or all base faces of the projections are arranged.

This choice of the projections ensures that, even with a simpler four-axis machine, planes in which the projections lie can be set up at a plurality of angles, for example plus/minus 45° to a machining axis of the machine, since due to the tapered configuration of the projections in the direction toward a machining tool, no undercuts exist in the closed mold structure relative to this tool.

In order to develop the greatest possible angular range, the side faces of pyramidal or tapered projections are at an angle of 45° relative to their base surface or the aforementioned plane, in which the projections are arranged. Then without the production of undercuts the plane in which the projections are arranged can be inclined by up to 45° to a machining axis of the machining apparatus, in particular to the machining axis, in the direction of which a tool of the machine is moved toward a blank or moved back.

In this way the invention provides that, even with a machining apparatus that has only four or even only three axes, it is possible to provide such positions of guide passages that in the past, according to the prior art, were only possible with more complicated five-axis machines.

Furthermore, the invention has the advantage that an attending dentist can, for example, use prefabricated blanks that only have to be brought into a required shape by a machining apparatus that can take place very quickly on site in the dental office.

Thus for this purpose the invention can provide, for example, that a mounting body blank comprises a block of material that can be removed for example by cutting, such as for example a plastic, and an adapter is arranged on or in the block. Also the invention can provide a passage element blank having a block of a material that can be removed in particular by cutting, such as for example a plastic, and on or in the block a guide passage is formed, for example, in the manner of a metallic sleeve, in particular where furthermore such a passage member blank also has an adapter for connection to the aforementioned mounting body blank or the adapter thereof, and this adapter can be formed, for example, by the guide passage itself.

Furthermore, the invention can also provide that a passage element blank has orientation elements, such as for example notches, in an end face of the guide passage or around the guide passage. When, for example, an adapter of a mounting body blank has complementary tabs, for example around an adaptor pin, a defined angular position between the passage element blank and the mounting body blank can be achieved when they are mounted to one another. Furthermore, however, the aforementioned notches on a passage element blank can also be employed in order to screw the shank of a later implant into the jawbone in a predefined angular position relative to the rotation.

The invention may also provide that there is a set of blanks of the aforementioned types in which the relative location between an adapter or a guide passage with respect to a grippable element for fastening of the blank to a machining apparatus is different. Depending upon the demand or the required positioning of the guide passage it may be reasonable here to be able to use differently prefabricated blanks with the different angular positions relative to the grippable element.

BRIEF DESCRIPTION OF THE DRAWING

An embodiment of the invention is described in greater detail below with reference to the following drawings.

SPECIFIC DESCRIPTION OF THE INVENTION

In the present case an impression element 1 is fitted on a plaster model of the patient's jaw structure. Obviously it is possible also to fasten the impression element 1 specifically to the patient's jaw, for example in order to x-ray the jaw.

For this purpose, a radiological reference, for example an X-ray reference 2, can be arranged as an arc in the vestibular region on the impression element 1 that itself may be formed, for example, as a deep-drawn film or also as a hardened impression compound, and this reference 2 here has radiopaque metal pins 3 that extend upward from the surface of the arcuate reference.

According to the invention the arcuate reference 2 with the metal pins 3 here also forms a fastening element 2 for the later mounting on the mounting plate, or an accessory arranged thereon, as described below.

Here the invention can provide in the usual way that by radiological recording, for example by digital volume tomography, the patient's jaw can be virtually displayed to enable the dentist to define for an implant to be placed with reference to the local conditions of the jawbone a guide passage through which a drilling tool is later guided.

According to the invention such a guide passage is fastened on the impression element 1 and as a result overall a drilling template is formed in the context of the invention.

Naturally the invention can provide not only a way to arrange a single guide passage on such an impression element 1, but in principle a plurality or any number of guide passages, in particular since according to the invention no supporting tooth structures are required.

Figure 1:
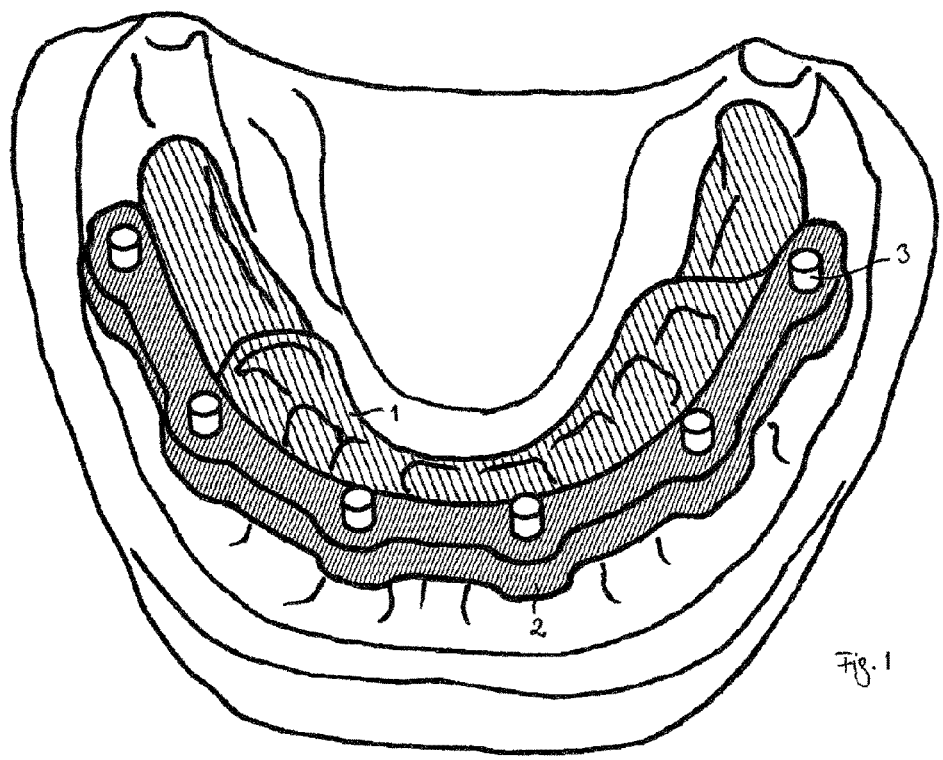
FIG. 1 is a plan view of an impression element that has a negative impression of a patient's jaw structure.
Figure 2:
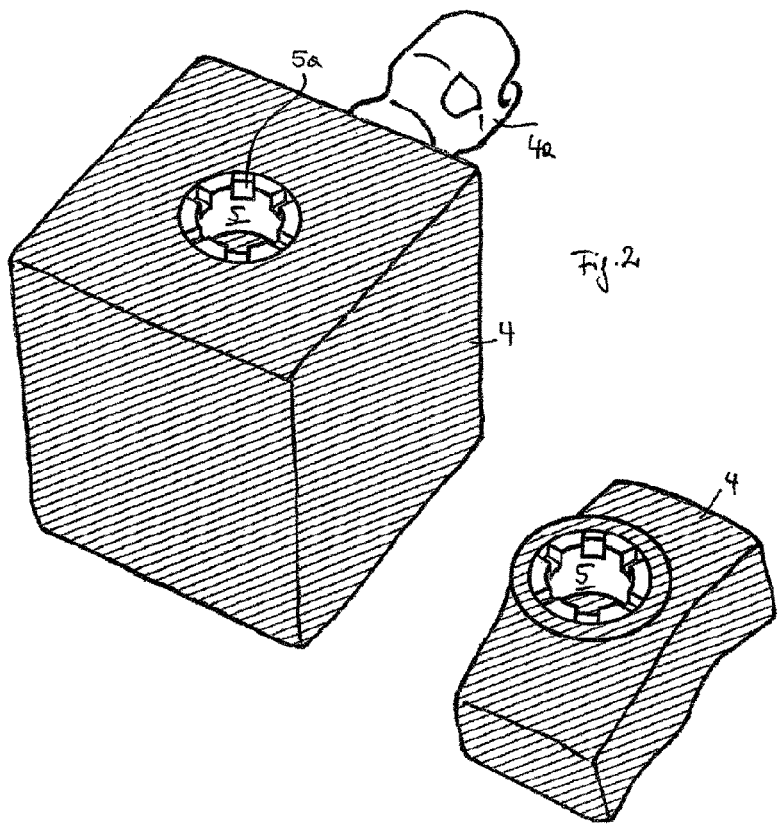
FIG. 2 shows on the left side a passage element before machining and on the right side the finish-machined passage element.

FIG. 2 shows on the left side a passage element 4 as a block, for example a cubical or rectangular block of a material such as plastic that can be machined, for example by cutting. The block has on one of its side faces a grippable element 4a by which the block can be anchored in a machining apparatus for the envisaged machining.

As an essential feature of the invention the blank of the passage element 4 has on one of its side faces a metallic sleeve forming a guide passage 5 extending from the surface of the passage element or blank 4 into its depth.

Furthermore, FIG. 2 shows that the sleeve forming the passage 5 has an array of notches 5a angularly equispaced around its end face. FIG. 2 shows on the right side a finish-machined passage element 4 after machining by a machining apparatus.

This can be provided in order to remove excess material from the blank, for example if the space conditions in the jaw region require it or to fix the location of the end face of the passage 5 exactly as required relative to the impression element and thus to define the later drilling depth.

In principle the invention can also provide for the use of passage elements 4 that do not have to undergo any machining before further fastening according to the invention to the impression element by a mounting body to be described below.

Figure 3:
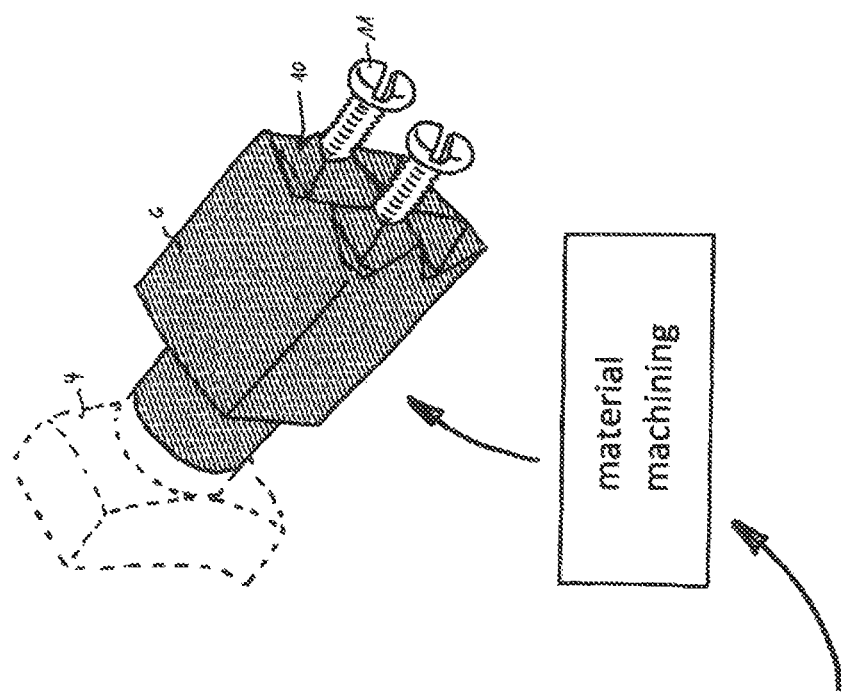
FIG. 3 are views of a blank of a mounting body with a substantially rectangular or cubical configuration after machining by a machining apparatus.
Figure 3:
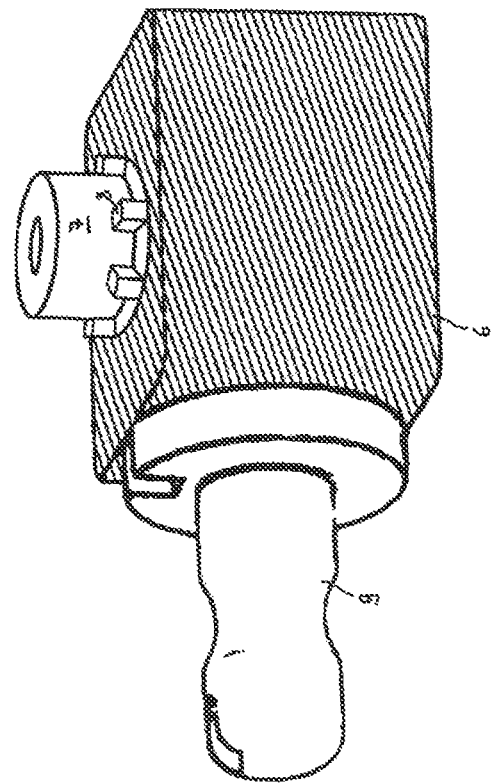

FIG. 3 is an overview of a blank of a mounting body 6 with a substantially rectangular or cubical configuration, and an adapter 7 projecting from one of the side faces of the blank. This adapter 7 corresponds to the guide passage 5 of the passage element, and tabs 8 complementarily fitting with the notches 5a are also provided here around the adapter 7.

In this example adaptation is understood to mean that the adapter 7 can be inserted substantially without play to the guide passage 5. Thus the possibility exists of attaching a passage element 4 in a defined situation on a mounting body blank 6, in particular after machining thereof.

As described in FIG. 2 with respect to the passage element, the blank 6 illustrated here also has a grippable element 9 that can be used to hold such a blank in a machining apparatus. Blanks with different orientations can be inserted between the grippable element 9 and the adapter 7.

Figure 4:
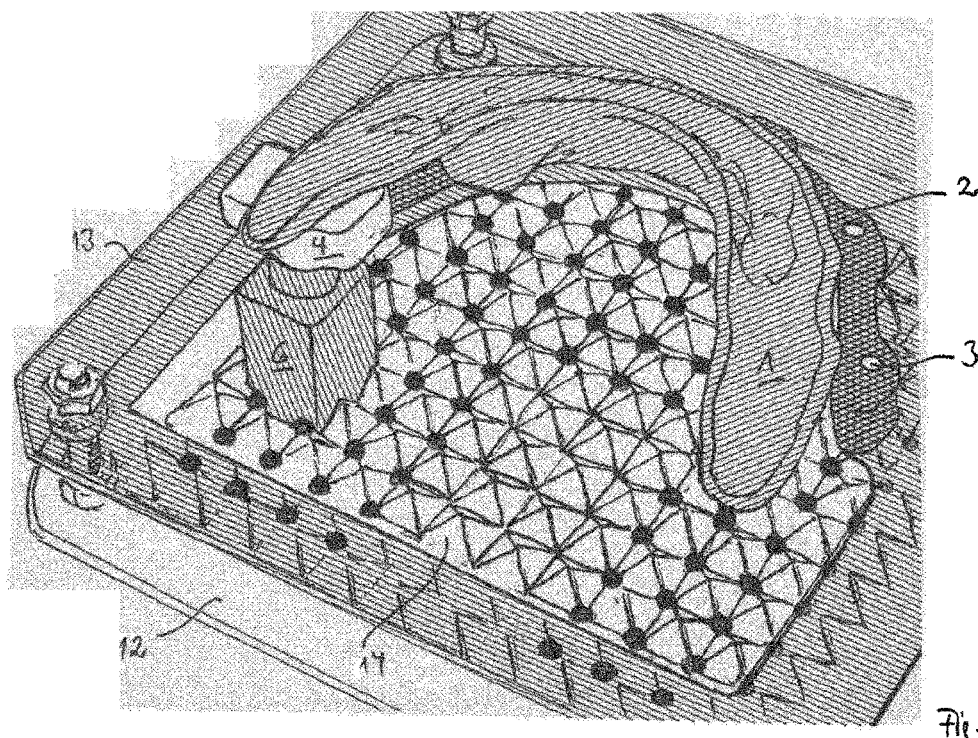
FIG. 4 shows the finished passage element and mounting body installed on a mounting structure.

According to the invention, as shown in FIG. 4, a mounting body 6 is manufactured from the mounting body blank in accordance with ascertained positional data for the guide passage 5 and has a closed mold mounting structure 10 that in the present case is designed as pyramidal projections each with four equal side faces. FIG. 4 shows that threaded bores with screws 11 that serve for later fastening are formed in these structures. According to FIG. 4 the passage element 4 is fastened on the mounting body 6 by insertion of the adapter 7 of the mounting body 6 into the guide passage 5. In this way the passage element 4 and the mounting body 6 form a component pair.

Figure 5:
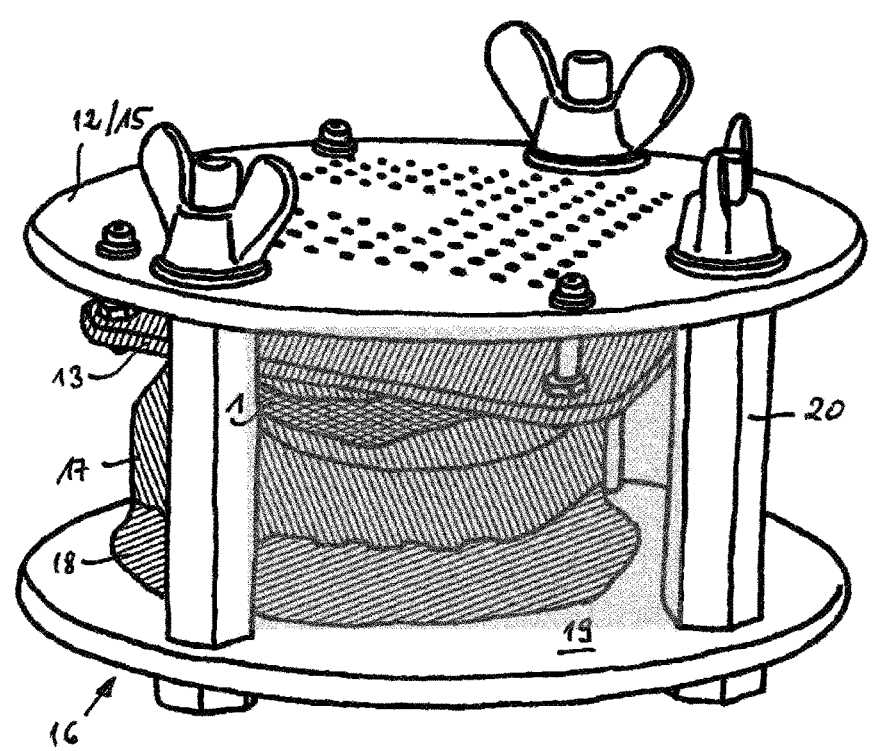
FIG. 5 shows the fully assembled system of this invention.

With regard to the situation of the projections that are pyramidal in this embodiment and the plane in which these projections, in particular the tips or the base faces thereof, are located, the closed mold mounting structure 10 is mounted on the mounting body in such a way that, as FIG. 5 shows, after fastening to a predetermined location on a mounting plate 12 this mounting body 6 positions the guide passage 5 of the sleeve 4 in the correctly required location relative to the impression element 1 fastened by the metal pins 3 on the mounting plate 12, in this case indirectly by a planar accessory 13 arranged parallel thereto but spaced therefrom.

The planar, preferably frame-like accessory 13 has a row of unillustrated holes that are arrayed complementarily to the metal pins 3, so that the impression element 1 can be fastened by the fastening element 2 in an opposing position spaced from the mounting plate 12.

The mounting body 6 fitted with its mounting structure 10 is in closed mold engagement with complementary pyramidal structure 14 projecting from the mounting plate 12 in this embodiment. It can be seen here that the pyramidal projections are in a uniform two-dimensional array, in particular so that their bases are immediately next to one another.

The pyramidal projections of the mounting structure on the mounting body 6 and the structure 14 on the mounting plate are formed identically complementary to one another here, so that in the uniform array a mounting body 6 with the mechanically produced mounting structure arranged thereon can be fastened in a closed mold manner on the structure 14 of the mounting plate.

The position of the mounting body on the structure of the mounting plate required for the correct location of the guide passage can be calculated, for example, by software in the uniform array and can be output to the user so that the attending dentist finds the correct position for the mounting on the plate. The plate 12 is formed in the structure 14 with a plurality of holes through which the screws 11 shown in FIG. 4 can be screwed into the mounting block from the underside of the mounting plate 12 in order to fasten the mounting block securely in the structure 14.

FIG. 5 shows that the passage element 4 adopts a position relative to the impression element 1 that was predetermined by the preceding determination of position of the virtual guide passage and the manufacture of the mounting body 6.

Alternatively, the mounting plate 12 can be secured relative to the impression element by a frame assembly 16 illustrated in FIG. 6, and the accessory 13 and the X-ray reference with metal pins 3 become unnecessary for the connection, and in particular can be removed. The frame comprises a base plate 19 and a cover plate 15 that are kept at a desired spacing and preferably parallel to one another by spacers 20.

For the mounting a model 17 of the jaw, for example by a base 18 on a base plate 19 of the frame 16, the above-mentioned mounting plate 12 can be replaced by the cover plate 15 of the frame assembly. In this case the cover plate 15 has the same closed mold structure in the same position on its underside as the mounting plate 12 described above. The accessory element 13 can be fastened in the same way and in the same position on the cover plate 15 as on the mounting plate 12. In particular, the previously described mounting plate 12 can be designed so that it corresponds to the cover plate 15, and thus a replacement is unnecessary.

After the positioning of the model 17 with the fitted impression element 1 on the base plate by the fastening element on the impression element and the engagement thereof in the accessory element 13, the accessory element 13 can be removed. In particular, in this respect the positioning of the model on the base plate is fixed.

With respect to FIG. 5 and alternatively in the embodiment of FIG. 6 it is now possible to secure the passage element 4 with the guide passage 5, for example, by an adhesive on the impression element 1, so that the drilling template to be produced according to the invention is formed from the combination of the guide passage element 4 and the impression element 1 then formed. For this purpose, the passage element 4 is separate from the mounting block 6.

The attending dentist can insert the impression element 1 in a patient to be treated, and then the guide passage for guiding the drill for placement of an implant shank is accessible for the dentist.

Furthermore, the invention can also provide, for example, that holes for cooling during the drilling operation are introduced into a blank of a guide passage element by a machining apparatus. Such cooling holes can, for example, intersect the guide passage.

In particular FIG. 5 shows clearly that in principle any number of passage elements 4 can be placed along the arcuate extension of the impression element 1.

It is also evident here as a further advantage that for placement of guide passages no support structures in the form of existing teeth have to be formed on a jaw structure. Therefore, the method according to the invention is, for example, also suitable for providing implants for completely toothless jaws or jaw portions having a reduced number of teeth.

The invention claimed is:

1. A method of making a dental drilling template shaped to the jaw structure of a patient, the drilling template having at least one guide passage for guiding a drilling tool, wherein
an impression element is produced with a negative impression of the jaw structure of a patient to be treated,
the impression element is provided with a radiological reference and positioned in or on the patients jaw region,
the jaw of a patient is radiologically recorded and positional data of an implant and the guide passage required therefor defined relative to the reference provided on the impression element on the basis of displayed data of a virtual jaw model,
the guide passage is positioned in accordance with the positional data on the impression element,
a mounting body having a fitting adapter and adapted to the required position of the guide passage is produced by material machining by a machining apparatus,
a form fitting mounting structure that is periodic in at least two directions is produced on the mounting body during its production in accordance with the positional data,
a passage element equipped with the guide passage in the form of a metallic sleeve, and having a fitting area that corresponds to the fitting adapter of the mounting body, is secured to the produced mounting body,
a subassembly formed by the interconnected mounting body and the passage element is fixed by the form fitting mounting structure of the mounting body in a position calculated in accordance with the positional data on a corresponding form fitting structure of a mounting plate,
the impression element is secured by a securing element opposite the mounting plate, and
the passage element is secured to the impression element by an adhesive and by detaching it from the mounting body so that the impression element becomes part of the drilling template.

2. The method according to claim 1, wherein as a function of the positional data a passage element is produced from a passage element blank already comprising the guide passage by removal of material by a machining apparatus or is produced at least partially by generative manufacture.

3. The method according to claim 2, wherein the machining of the passage element blank and/or mounting body blank takes place with a 4-axis milling machine in which a respective blank is gripped by a grippable element arranged on the blank.

4. The method according to claim 1 wherein the impression element is fastened directly or indirectly on the mounting plate with a fastening element having a radiological reference in the form of metal elements.

5. The method according to claim 1, wherein by tomographic radiological digital volume tomography, with the aid of software a virtual model of a patient's jaw is produced and a virtual guide passage is positioned relative to the virtual jaw model and to the radiological reference, positional data that determine the position of the closed mounting structure on the mounting body being formed from the positional data of the virtual guide passage.

6. The method according to claim 5, wherein the closed mounting structure on the mounting body and/or the closed mounting structure on the mounting plate is formed as tapered projections arranged periodically adjacent to one another in at least two directions as pyramidal projections with at least three side faces inclined relative to one another, or as conical projections.

7. A mounting body blank for use in a method according to claim 1, the blank comprising a block of a material that can be removed by cutting, wherein an adapter is arranged on/in the block.

8. A set of blanks according to claim 7, wherein the relative location between an adapter or a guide passage with respect to a grippable element for fastening of the blank in a machining apparatus is different.

9. A passage element blank for use in a method according to claim 1, the passage element comprising: a block of a material that can be removed, wherein a guide passage is arranged on/in the block, wherein the guide passage forms an adapter.

10. The passage element blank according to claim 9, wherein orientation elements are arranged as notches or grooves in an end face of the guide passage or around the guide passage.

* * * * *